United States Patent
Burns et al.

(10) Patent No.: US 7,354,935 B2
(45) Date of Patent: Apr. 8, 2008

(54) RADIOLABELED NEUROKININ-1 RECEPTOR ANTAGONISTS

(75) Inventors: H. Donald Burns, Harleysville, PA (US); Wai-si Eng, Maple Glen, PA (US); Raymond E. Gibson, Holland, PA (US); Terence G. Hamill, Lansdale, PA (US)

(73) Assignee: Merck & Co. Inc., Rahway, NJ (US)

( * ) Notice: Subject to any disclaimer, the term of this patent is extended or adjusted under 35 U.S.C. 154(b) by 541 days.

(21) Appl. No.: 10/528,888

(22) PCT Filed: Sep. 19, 2003

(86) PCT No.: PCT/US03/29707

§ 371 (c)(1), (2), (4) Date: Mar. 23, 2005

(87) PCT Pub. No.: WO2004/029024

PCT Pub. Date: Apr. 8, 2004

(65) Prior Publication Data

US 2005/0214204 A1    Sep. 29, 2005

Related U.S. Application Data

(60) Provisional application No. 60/413,223, filed on Sep. 24, 2002.

(51) Int. Cl.
*A61K 31/445* (2006.01)
*C07D 401/12* (2006.01)

(52) U.S. Cl. ...................... 514/326; 546/201
(58) Field of Classification Search ............. 514/326; 546/201

See application file for complete search history.

(56) References Cited

U.S. PATENT DOCUMENTS 6,241,964 B1    6/2001    Burns et al.

FOREIGN PATENT DOCUMENTS

WO    WO 96/21661    7/1996

OTHER PUBLICATIONS

Database CAPLUS on STN (Columbus OH, USA) No. 1998:141375, Ding et al. "probing the biochemical basis of the pet image," Abstract, Mar. 29, 1998.
Database CAPLUS on STN (Columbus OH, USA) No. 1995: 924600, Ding et al. "Mechanistic pet studies of F-18 labeled catecholamines in living baboon heart," Abstract, Aug. 20-24, 1995.

*Primary Examiner*—Celia Chang
(74) *Attorney, Agent, or Firm*—J. Eric Thies; William Krovatin

(57) ABSTRACT

The present invention is directed to radiolabeled neurokinin-1 receptor antagonists which are useful for the labeling and diagnostic imaging of neurokinin-1 receptors in mammals.

6 Claims, No Drawings

RADIOLABELED NEUROKININ-1 RECEPTOR ANTAGONISTS

CROSS REFERENCE TO RELATED APPLICATIONS

This application is a U.S. National Phase application under 35 U.S.C. § 371 of PCT Application No. PCT/US03/29707, filed Sep. 19, 2003, which claims priority under 35 U.S.C. § 119 from U.S. Application No. 60/413,223, filed Sep. 24, 2002.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation which is capable of detecting radiation emitted from radiotracers administered to such living subjects. The information obtained can be reconstructed to provide planar and tomographic images which reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lifes of 20, 110, 2 and 10 min. respectively. Since the half-lives of these radionuclides are so short, it is only feasible to use them at institutions which have an accelerator on site for their production, thus limiting their use. Several gamma emitting radiotracers are available which can be used by essentially any hospital in the U.S. and in most hospitals worldwide. The most widely used of these are $^{18}F$, $^{99m}Tc$, $^{201}Tl$ and $^{123}I$.

In the past decade, one of the most active areas of nuclear medicine research has been the development of receptor imaging radiotracers. These tracers bind with high affinity and specificity to selective hormone receptors and neuroreceptors. The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. Substance P (also called "SP" herein) is a naturally occurring undecapeptide belonging to the tachykinin family of peptides, the latter being so-named because of their prompt contractile action on extravascular smooth muscle tissue. In addition to SP the known mammalian tachykinins include neurokinin A and neurokinin B. The current nonmenclature designates the receptors for SP, neurokinin A, and neurokinin B as NK-1, NK-2, and NK-3, respectively. Neurokinin-1 (NK-1; substance P) receptor antagonists are being developed for the treatment of a number of physiological disorders associated with an excess or imbalance of tachykinins, and in particular substance P. Substance P has been implicated in gastrointestinal (GI) disorders and diseases of the GI tract, such as emesis, and in psychiatric disorders, such as depression. The compound [2-fluoromethoxy-5-(5-trifluoromethyl-tetrazol-1-yl)-benzyl]-([2S,3S]-2-phenyl-piperidin-3-yl)-amine is disclosed in PCT Patent Publication WO 96/21661 as a tachykinin antagonist. U.S. Pat. No. 6,241,964 discloses the compound [$^{18}F$][2-fluoromethoxy-5-(5-trifluoromethyl-tetrazol-1-yl)-benzyl]-([2S,3S]-2-phenyl-piperidin-3-yl)-amine.

PET (Positron Emission Tomography) radiotracers and imaging technology may provide a powerful method for clinical evaluation and dose selection of neurokinin-1 receptor antagonists. Using a fluorine-18 or carbon-11 labeled radiotracer that provides a neurokinin-1 receptor-specific image in the brain and other tissues, the dose required to saturate neurokinin-1 receptors can be determined by the blockade of the PET radiotracer image in humans. The rationale for this approach is as follows: efficacy of a neurokinin-1 receptor antagonist is a consequence of the extent of receptor inhibition, which in turn is a function of the degree of drug-receptor occupancy.

It is, therefore, an object of this invention to develop radiolabeled neurokinin-1 receptor antagonists that would be useful not only in traditional exploratory and diagnostic imaging applications, but would also be useful in assays, both in vitro and in vivo, for labeling the neurokinin-1 receptor and for competing with unlabeled neurokinin-1 receptor antagonists and agonists. It is a further object of this invention to develop novel assays which comprise such radiolabeled compounds.

SUMMARY OF THE INVENTION

The present invention is directed to certain radiolabeled neurokinin-1 receptor antagonists. The present invention is further concerned with methods for the use of such radiolabeled neurokinin-1 receptor antagonists for the labeling and diagnostic imaging of neurokinin-1 receptors in mammals.

DETAILED DESCRIPTION OF THE INVENTION

The present invention is directed to certain radiolabeled neurokinin-1 receptor antagonists. In particular, the present invention is directed to a compound of the formula:

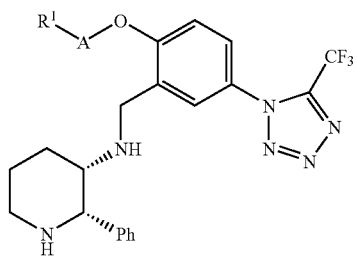

wherein:
A is —$CD_2$— or —$CH_2CH_2$—;

$R^1$ is a radionuclide selected from the group consisting of: $^3H$, $^{11}C$, $^{18}F$, $^{125}I$, $^{82}Br$, $^{123}I$, $^{131}I$, $^{75}Br$, $^{15}O$, $^{13}N$, $^{211}At$ and $^{77}Br$;

and pharmaceutically acceptable salts thereof.

In another embodiment of the present invention $R^1$ is $^{11}C$ or $^{18}F$.

In another embodiment of the present invention $R^1$ is $^{18}F$.

In another embodiment the present invention is directed to the compound

[$^{18}F$][2-fluorodideuteromethoxy-5-(5-trifluoromethyl-tetrazol-1-yl)-benzyl]-([2S,3S]-2-phenyl-piperidin-3-yl)-amine which may be depicted as:

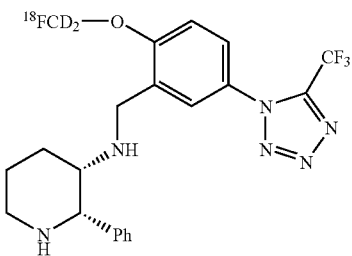

In another embodiment the present invention is directed to the compound

[$^{18}F$][3-fluoroethoxy-5-(5-trifluoromethyl-tetrazol-1-yl)-benzyl]-([2S,3S]-2-phenyl-piperidin-3-yl)-amine which may be depicted as:

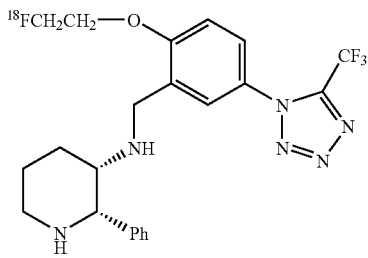

As appreciated by those of skill in the art, "D" or deutero as used herein are intended to include the isotope $^2H$ or deuterium.

The present invention is also directed to a radiopharmaceutical composition which comprises a compound of the present invention and at least one pharmaceutically acceptable carrier or excipient.

The present invention is also directed to a method for labeling neurokinin-1 receptors in a mammal which comprises administering to a mammal in need of such labeling an effective amount of the radiolabeled compound of the present invention.

The present invention is also directed to a method for diagnostic imaging of neurokinin-1 receptors in a mammal which comprises administering to a mammal in need of such diagnostic imaging an effective amount of the radiolabeled compound of the present invention.

The present invention is also directed to a method for diagnostic imaging of tissues bearing neurokinin-1 receptors in a mammal which comprises administering to a mammal in need of such diagnostic imaging an effective amount of the radiolabeled compound of the present invention.

The present invention is also directed to a method for the diagnostic imaging of substance P binding sites in tissues of a mammalian species which comprises administering to the mammalian species in need of such diagnostic imaging an effective amount of the radiolabeled compound of the present invention.

The present invention is also directed to a method for diagnostic imaging of the brain in a mammal which comprises administering to a mammal in need of such diagnostic imaging an effective amount of the radiolabeled compound of the present invention.

The present invention is further directed to a method for the detection or quantification of neurokinin-1 receptors in mammalian tissue which comprises administering to a mammal in which such quantification is desired an effective amount of the radiolabeled compound of the present invention.

In a preferred embodiment of the methods of the present invention, the mammal is a human.

Suitable radionuclides that may be incorporated in the instant compounds include $^3H$ (also written as T), $^{11}C$, $^{18}F$, $^{125}I$, $^{82}Br$, $^{123}I$, $^{131}I$, $^{75}Br$, $^{15}O$, $^{13}N$, $^{211}At$ or $^{77}Br$. The radionuclide that is incorporated in the instant radiolabeled compounds will depend on the specific analytical or pharmaceutical application of that radiolabeled compound. Thus, for in vitro labeling of neurokinin receptors and competition assays, compounds that incorporate $^3H$, $^{125}I$ or $^{82}Br$ will generally be most useful. For diagnostic imaging agents, compounds that incorporate a radionuclide selected from $^{11}C$, $^{18}F$, $^{123}I$, $^{131}I$, $^{75}Br$, $^{76}Br$ or $^{77}Br$ are preferred. In certain applications incorporation of a chelating radionuclide such as $Tc^{99m}$ may also be useful. In the present invention, $^{18}F$ is particularly preferred over $^{11}C$ because with the longer half-life of $^{18}F$, imaging can be carried out long enough to allow a more specific signal to develop and improved conditions for receptor quantification studies.

Radiolabeled neurokinin-1 receptor antagonists, when labeled with the appropriate radionuclide, are potentially useful for diagnostic imaging, basic research, and radiotherapeutic applications. Specific examples of possible diagnostic imaging and radiotherapeutic applications, include determining the location, the relative activity and/or the abundance of neurokinin-1 receptors, radioimmunoassay of neurokinin-1 receptor antagonists, and autoradiography to determine the distribution of neurokinin-1 receptors in a mammal or an organ or tissue sample thereof.

In particular, the instant radiolabeled neurokinin-1 receptor antagonists when labeled with the positron emitting radionuclide, F-18, are useful for positron emission tomographic (PET) imaging of neurokinin-1 receptors in the brain of living humans and experimental animals. This radiolabeled neurokinin-1 receptor antagonists may be used as research tools to study the interaction of unlabeled neurokinin-1 antagonist with neurokinin-1 receptors in vivo via competition between the labeled drug and the radiolabeled compound for binding to the receptor. This type of study is useful for determining the relationship between neurokinin-1 receptor occupancy and dose of unlabeled neurokinin-1 receptor antagonist, as well as for studying the duration of blockade of the receptor by various doses of the unlabeled neurokinin-1 receptor antagonist. As a clinical tool, the radiolabeled neurokinin-1 receptor antagonists may be used to help define a clinically efficacious dose of a neurokinin-1 receptor antagonist. In animal experiments, the radiolabeled neurokinin-1 receptor antagonists can be used to provide information that is useful for choosing between potential drug candidate for selection for clinical development. The radiolabeled neurokinin-1 receptor antagonists may also be used to study the regional distribution and concentration of neurokinin-1 receptors in the living human brain, as well as the brain of living experimental animals and in tissue samples. The radiolabeled neurokinin-1 receptor antagonists may also be used to study disease or pharmacologically related changes in neurokinin-1 receptor concentrations.

For example, positron emission tomography (PET) tracer such as the present radiolabeled neurokinin-1 receptor antagonists which can be used with currently available PET technology to obtain the following information: relationship between level of receptor occupancy by candidate neurokinin-1 antagonist and clinical efficacy in patients; dose selection for clinical trials of neurokinin-1 antagonists prior to initiation of long term clinical studies; comparative potencies of structurally novel neurokinin-1 antagonists; investigating the influence of neurokinin-1 antagonists on in vivo receptor affinity and density during the treatment of clinical targets with neurokinin-1 receptor antagonists and other agents; changes in the density and distribution of neurokinin-1 receptors during e.g. psychiatric diseases in their active stages, during effective and ineffective treatment and during remission; and changes in neurokinin-1 receptor expression and distribution in CNS disorders (e.g. depression, head injury and Parkinson's disease); imaging inflammatory conditions where substance P is involved and/or neurokinin-1 receptors are upregulated; imaging neurodegenerative disease such as Alzheimer's Disease, multiple sclerosis, and the like that have an inflammatory component; imaging cancerous tumors which express neurokinin-1 receptors; assessing cancerous tumors which express neurokinin-1 receptors to indicate the distribution of such tumors or provide an index of their growth.

For the use of the instant compounds as exploratory or diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

Radiotracers labeled with short-lived, positron emitting radionuclides are almost always administered via intravenous injection within less than one hour of their synthesis. This is necessary because of the short half-life of the radionuclides involved (20 and 110 minutes for C-11 and F-18 respectively).

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

A minimum dosage level for the unlabeled neurokinin-1 receptor antagonist is about 1 mg per day, preferably about 5 mg per day and especially about 10 mg per day. A maximum dosage level for the neurokinin-1 receptor antagonist is about 1500 mg per day, preferably about 1000 mg per day and especially about 500 mg per day. It will be appreciated that the amount of the neurokinin-1 receptor antagonist required for use in the present invention will vary not only with the particular compounds or compositions selected but also with the route of administration, the nature of the condition being treated or studied, and the age and condition of the patient, and will ultimately be at the discretion of the patient's physician or pharmacist.

When a radiolabeled neurokinin-1 receptor antagonist according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1-5 mCi.

In one exemplary application, administration occurs in an amount of radiolabeled compound of between about 0.005 µg/kg of body weight to about 50 µg/kcg of body weight per day, preferably of between 0.02 µg/kg of body weight to about 3 µg/kg of body weight. A particular analytical dosage that comprises the instant composition includes from about 0.5 µg to about 100 µg of a labeled neurokinin-1 receptor antagonist. Preferably, the dosage comprises from about 1 µg to about 50 µg of a radiolabeled neurokinin-1 receptor antagonist.

The following illustrative procedure may be utilized when performing PET imaging studies on patients in the clinic. The patient is premedicated with unlabeled neurokinin-1 receptor antagonist (at doses 300, 100, or 30 mg/day) for 2 weeks prior to the day of the experiment and is fasted for at least 12 hours allowing water intake ad libitum. A 20 G two inch venous catheter is inserted into the contralateral ulnar vein for radiotracer administration.

The patient is positioned in the PET camera and a tracer dose of [$^{15}$O]H$_2$O administered via i.v. catheter. The image thus obtained is used to insure that the patient is positioned correctly to include the brain or other areas of interest. Subsequently the [$^{18}$F] neurokinin-1 receptor antagonist (<20 mCi) is administered via i.v. catheter. Following the acquisition of the total radiotracer image, an infusion is begun of the neurokinin-1 receptor antagonist which is being clinically evaluated at one of three dose rates (0.1, 1 or 10 mpk/day). After infusion for 2.5 hrs, the [$^{18}$F] neurokinin-1 receptor antagonist is again injected via the catheter. Images are again acquired for up to 90 min. Within ten minutes of the injection of radiotracer and at the end of the imaging session, 1 ml blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of receptor antagonist or in the presence of the clinical candidate at the various infusion doses examined. Data are expressed as radioactivity per unit time per unit volume (µCi/cc/mCi injected dose). Inhibition curves are generated from the data obtained in a region of interest obtained starting at 70 minutes post-injection of radiotracer. At this time, clearance of non-specific binding has reached steady state. The ID$_{50}$ values are obtained by curve fitting the dose-rate/inhibition curves with equation iii:

$$B = A_0 - A_0 * I / (ID_{50} + I) + NS \quad \text{(iii)}$$

where B is the %-Dose/g of radiotracer in tissues for each dose of clinical candidate, A$_0$ is the specifically bound radiotracer in a tissue in the absence of a neurokinin-1 receptor antagonist, I is the injected dose of antagonist, ID$_{50}$ is the dose of compound which inhibits 50% of specific radiotracer binding to a neurokinin receptor, and NS is the amount of non-specifically bond radiotracer.

Gamma Camera Imaging

Two rats are anesthetized (ketamine/ace-promazine), positioned on the camera head, and their tail veins canulated for ease of injection. One rat is preinjected with an unlabeled neurokinin-1 receptor antagonist (10% EtOH/27% PEG/63% H$_2$O) 30 min. prior to injection of radiotracer to demonstrate non-specific binding. 150 uCi/rat of an $^{18}$F labeled neurokinin-1 receptor antagonist is injected via its tail vein, and the catheters flushed with several mls of normal saline. Acquisition of images is started as the radiotracer was injected. Sixty, one minute images are acquired and the rats are subsequently euthanized with sodium pentobarbital. Regions of interest (ROIs) are drawn on the first image which includes the brain, then used to analyze the count rates in subsequent images. ROIs are defined to remain fairly clear during the course of the study, and are assumed to be representative of the entire organ. Count-rates are converted to %-dose/ROI by dividing the count-rate in the ROI by that of the whole rat, which is then multiplied by 100.

PET Imaging in Dogs

Female beagle dogs weighing 7.7-14.6 kg (11.0±2.3 kg) are premedicated with unlabeled neurokinin-1 receptor antagonist (at doses 300, 100, or 30 mg/day) for 2 weeks prior to the day of the experiment and are fasted for at least 12 hours allowing water intake ad libitum. A 20 G two inch venous catheter is placed into the right front leg ulnar vein through which anesthesia is introduced by sodium pentobarbital 25-30 mg/kg in 3-4 ml and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of [$^{15}$O]H$_2$O administered via i.v. catheter. The image thus obtained is used to insure that the dog is positioned correctly to include the brain and other areas of interest. Subsequently [$^{18}$F]-neurokinin-1 receptor antagonist (<20 mCi) is administered via i.v. catheter. Following the acquisition of the total radiotracer image, an infusion is begun of the unlabeled neurokinin-1 receptor antagonist at one of three dose rates (0.1, 1 or 10 mpk/day). After infusion for 2.5 hrs, [$^{18}$F]-neurokinin-1 receptor antagonist is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk another neurokinin-1 receptor antagonist is infused over 5 minutes. This dose has been determined to completely block radiotracer binding and thus is used to determine the maximum receptor-specific signal obtained with the PET radiotracer. At the conclusion of the study, animals are recovered and returned to animal housing.

For uninhibited distribution of radiotracer, regions of interest (ROIs) are drawn on the reconstructed image including the brain. These regions are used to generate time activity curves obtained in the absence of test compound or in the presence of test compound at the various infusion doses examined. Data are expressed as radioactivity per unit time per unit volume (µCi/cc/mCi injected dose). Inhibition curves are generated from the data obtained in a region of interest obtained starting at 70 min. post-injection of radiotracer. By this time, clearance of non-specific binding will have reached steady state. The ID$_{50}$ are were obtained by curve fitting the dose-rate/inhibition curves with equation iii, hereinabove.

The compounds of the present invention possess unexpected advantages with respect to the compound [$^{18}$F][2-fluoromethoxy-5-(5-trifluoromethyl-tetrazol-1-yl)-benzyl]-([2S,3S]-2-phenyl-piperidin-3-yl)-amine which is disclosed in U.S. Pat. No. 6,241,964.

[$^{18}$F][2-Fluorodideuteromethoxy-5-(5-trifluoromethyl-tetrazol-1-yl)-benzyl]-([2S,3S]-2-phenyl-piperidin-3-yl)-amine is metabolically more stable than [$^{18}$F][2-fluoromethoxy-5-(5-trifluoromethyl-tetrazol-1-yl)-benzyl]-([2S,3S]-2-phenyl-piperidin-3-yl)-amine. [$^{18}$F][2-

Fluorodideuteromethoxy-5-(5-trifluoromethyl-tetrazol-1-yl)-benzyl]-([2S,3S]-2-phenyl-piperidin-3-yl)-amine also possesses a longer plasma half-life than [$^{18}$F][2-fluoromethoxy-5-(5-trifluoromethyl-tetrazol-1-yl)-benzyl]-([2S,3S]-2-phenyl-piperidin-3-yl)-amine which results in relatively higher brain levels of the tracer.

[$^{18}$F][3-Fluoroethoxy-5-(5-trifluoromethyl-tetrazol-1-yl)-benzyl]-([2S,3S]-2-phenyl-piperidin-3-yl)-amine can be displaced from the NK1 receptor faster than [$^{18}$F][2-fluoromethoxy-5-(5-trifluoromethyl-tetrazol-1-yl)-benzyl]-([2S,3S]-2-phenyl-piperidin-3-yl)-am when unlabelled compounds are administered. A tracer with such properties as [$^{18}$F][3-fluoroethoxy-5-(5-trifluoromethyl-tetrazol-1-yl)-benzyl]-([2S,3S]-2-phenyl-piperidin-3-yl)-ami that is in equilibrium with the receptor gives a more accurate measurement of the true receptor occupancy because this occupancy changes over time.

Neurokinin-1 receptor antagonists which incorporate a radionuclide may be prepared by first synthesizing an unlabeled compound that optionally incorpoates a iodo or bromo moiety and then exchanging a hydrogen or halogen moiety with an appropriate radionuclide using techniques well known in the art. Alternately, a radiolabeled neurokinin-1 receptor antagonist may be prepared by alkylation with a radiolabeled alkylating agent. Syntheses of unlabeled neurokinin-1 receptor antagonist have been generally described in the patent publications cited hereinabove. Syntheses of particular neurokinin-1 receptor antagonists is described below. During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups its Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the order of carrying out the following reaction schemes may be varied to facilitate the reaction or to avoid unwanted reaction products.

The following examples are provided for the purpose of further illustration only and are not intended to be limitations on the disclosed invention.

EXAMPLE 1

(2S,3S)-(−)-3-Amino-2-phenylpiperidine

The title compound is prepared essentially as described below.

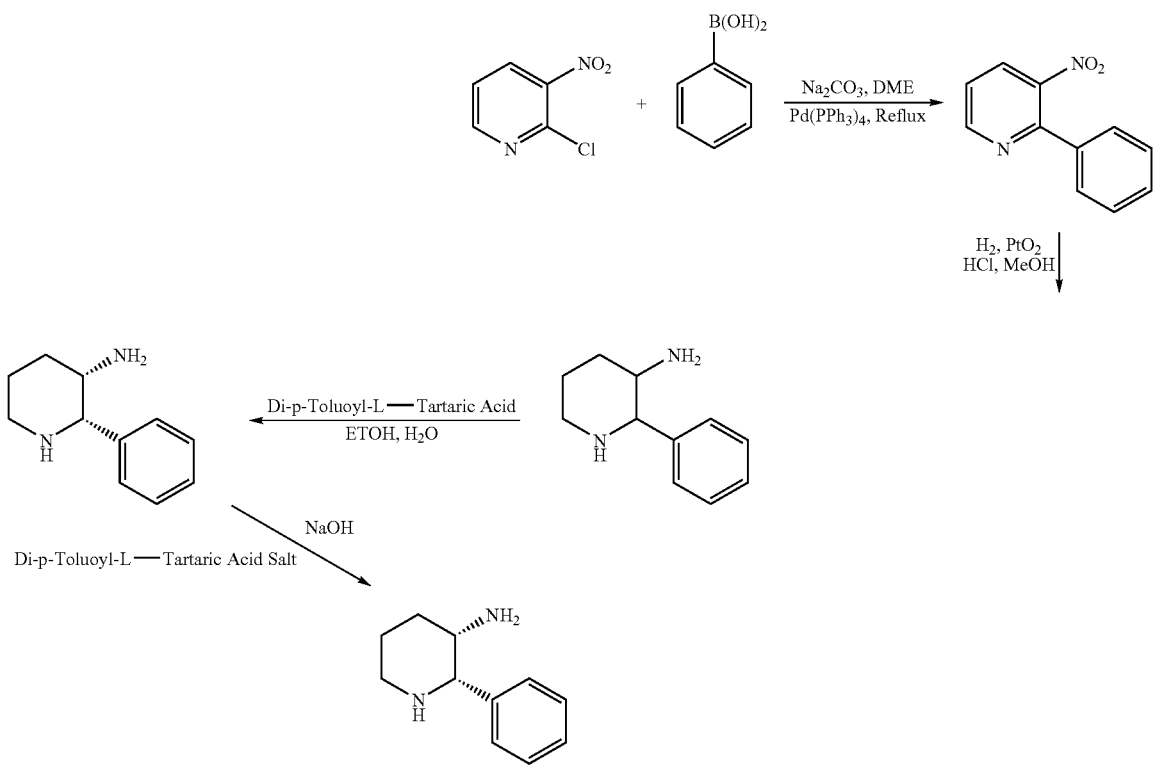

Step 1: 2-Phenyl-3-nitropyridine

A 5 L round bottom flask fitted with a condenser, mechanical stirrer and a nitrogen inlet was charged with 152.3 g (0.96 mol) of 2-chloro-3-nitropyridine and 1.65 L of 1,2-dimethoxyethane. The solution was degassed by bubbling nitrgen through the solution for 10 min and 56.7 g (0.49 mol, 0.05 equiv) of tetrakis(triphenylphosphine)-palladium (0) was added. The mixture was degassed for an additional 45 min during which time the catalyst dissolved leaving a clear dark red solution. A degassed solution of 180.3 g (1.48 mol, 1.54 equiv) of phenylboronic acid in 800 mL of absolute ethanol was added followed by 1.65 L of degassed 2M aqueous sodium carbonate solution. The cloudy mixture was heated to reflux, and refluxed for 1.5 h. While at reflux a yellow suspension formed. The suspension was cooled to ambient temperature, diluted with 1 L of ethyl acetate, and filtered through Celite®. The cake was washed with 2 L of ethyl acetate and the filtrate washed with water (2×3 L), saturated sodium bicarbonate solution (1×3 L), and saturated sodium chloride solution (1×3 L). The organic layer was dried with magnesium sulfate, filtered and the filtrate concentrated. The residue was dissolved in 1.5 L of ether, washed with 2.5N NaOH (2×500 mL) and brine (500 mL). The solution was dried with magnesium sulfate, filtered through 400 g of silica and the cake washed with additional ethyl acetate. The filtrate was concentrated to an oil which was chromatographed [5 kg Silica Gel 60, 70-230 mesh, hexanes/ethyl acetate 80:20 (12 L), 75:25 (8 L), 70:30 (11 L) and 60:40 (7 L)]. The product fractions were concentrated yielding 188.0 g (97% yield) of the title compound 2-phenyl-3-nitropyridine, as a pale yellow oil: $^1$H NMR (CDCl$_3$) δ 7.39-7.49 (m, 4H), 753-7.95 (m, 2H), 8.12 (m, 1H) 8.84 (m, 1H). MS (EI) m/z 200. Anal. Calcd for $C_{11}H_8N_2O_4$: C, 66.00; H, 4.03; N, 13.99. Found: C, 66.19; H, 4.09; N, 13.98.

Step 2: cis-2-Phenyl-3-aminopiperidine

A solution of 30 g (0.15 mol) of 2-phenyl-3-nitropyridine in 190 mL of methanol was hydrogenated using 5 g of platinum oxide with an initial pressure of 45 psi hydrogen. After 2 h, 50 mL of conc HCl was added, the vessel repressurized to 45 psi, and the reduction continued for an additional 6.25 h. The reaction was diluted with water (100 mL) and filtered. Three reactions were combined at this point and the combined cake washed with methanol (200 mL), water (100 mL), methanol (200 mL), water (100 mL), and methanol (200 mL). The filtrate was concentrated, the residue treated with 500 mL of 5N NaOH and extracted with ether (3×1 L) and methylene chloride (2×1 L). The combined extracts were dried with sodium sulfate, filtered and the filtrate concentrated to afford 80.9 g of a pale yellow oil. Chromatography (5 kg Silica Gel 60, 70-230 mesh, methylene chloride/methanol/ammonium hydroxide 92.5:7.5:0.75) afforded 62 g (78% yield) of cis-2-phenyl-3-aminopiperidine as a pale yellow oil: $^1$H NMR (CDCl$_3$) δ 1.35-1.55 (m, 4H), 1.65-1.98 (m, 3H), 2.75 (m, 1H), 2.95 (m, 1H), 3.8 (bs, 1H), 7.19-7.37 (m, 5H). MS (EI) m/z 176.

Step 3: [2S]-Phenyl-piperidin-[3S]-yl-amine[2R, 3R]-bis(4-methyl-benzyloxy)-succinate To a solution of 41 g (0.23 mol) of cis-2-phenyl-3-aminopiperidine in ethanol (3.25 L) and water (440 mL) at 60° C. was added 88 g (0.23 mol) of di-p-toluoyl-L-tartaric acid. The acid dissolved quickly leaving a clear pale yellow solution. After a few minutes a suspension formed. Heating was continued for 20 min. The suspension was allowed to cool, with stirring, to ambient temperature overnight. The product was collected by filtration, washed with ethanol (200 mL) and ether (200 mL) and air dried affording 60.0 g of the title compound (86% of theory). [α]$^{20}_D$=−54° (C=0.5, MeOH). HPLC analysis (Chiracel OD-R, 4.6×250 mm column, 0.5 mL/min 55:45 0.1% TFA-water/acetonitile 35° C., λ 245) showed the material had a very high optical purity with no detectable amount of the other enantiomer: Calcd for $C_{31}H_{34}N_2O_8$.:$H_2O$: C, 64.13; H, 6.25; N, 4.83. Found: C, 6.22; H, 6.33; N, 4.75. KF=3.48% (theory 3.1%).

Step 4: (2S,3S)-(−)-3-amino-2-phenylpiperidine

[2S]-Phenyl-piperidin-[3S]-yl-amiune[2R,3R]-bis(4-methyl-benzyloxy)-succinate (5 g, 8.33 mmol)) was partitioned between 100 mL of methylene chloride and 25 mL of 1N NaOH. The aqueous was re-extracted with 50 mL of methylene chloride and the combined organic layer dried with sodium sulfate, filtered and concentrated.

EXAMPLE 2

(2S,3S)-1-t-Butoxycarbonyl-2-phenyl-3-[2-hydroxy-5-(5'-trifluoromethyltetrazo-1-yl)phenylmethylene-amino]piperidine The title compound is prepared essentially as outlined below.

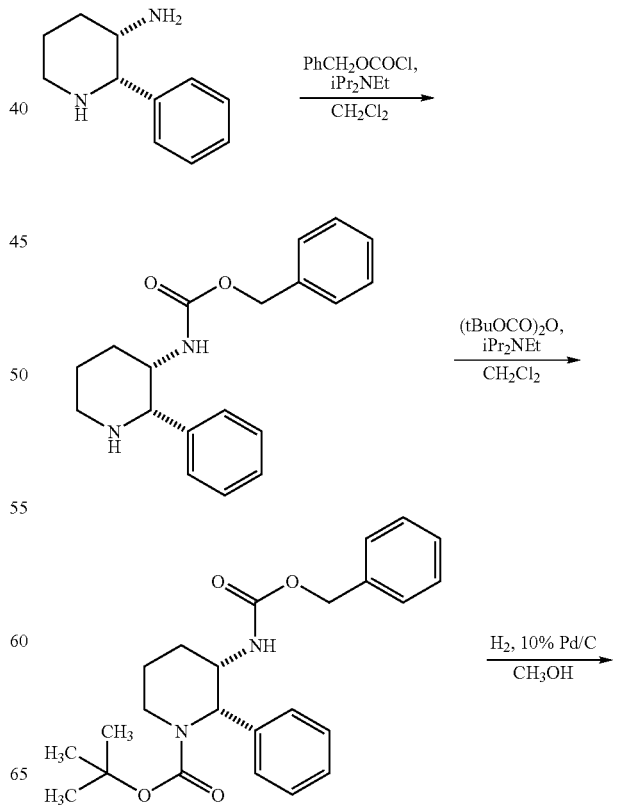

-continued

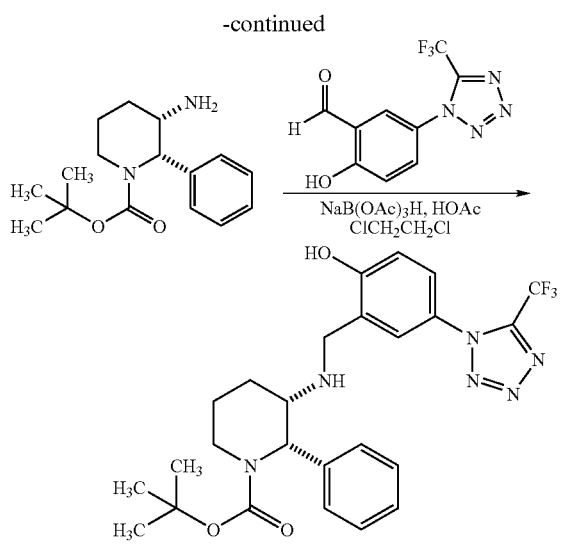

Step 1: (2S,3S)-3-Benzyloxycarbonylamino-2-phenylpiperidine

To a solution of (2S,3S)-(−)-3-amino-2-phenylpiperidine (152 mg, 0.86 mmole) (L-tartaric acid salt, $[\alpha]_D = -57.1$ (EtOH, c=0.1138)) in methylene chloride (10 mL) at room temperature was added benzyl chloroformate (0.123 mL, 0.86 mmole) and diisopropylethylamine (0.45 mL, 2.58 mmole). The reaction was stirred for 16 hours and was then diluted with methylene chloride and quenched by addition of water. The mixture was separated and the aqueous was reextracted with 2 additional aliquots of methylene chloride. The organic layers were successively washed with a portion of brine, dried over sodium sulfate, combined and evaporated. The residue was purified by flash chromatography (5% methanol in methylene chloride) to afford 214 mg (80%) of the title compound. NMR (CDCl$_3$): δ 1.55 (br. d, J=9 Hz, 1H), 1.6-1.9 (m, 2H), 2.02 (br. d, J=9 Hz, 1H), 2.79 (dd, J=9 and 10 Hz, 1H), 3.22 (dd, J=1 and 10 Hz, 1H), 3.91 (br. s, 1H), 4.01 (dd, J=1 and 8 Hz, 1H), 4.89 (s, 2H), 5.65 and 5.88 (2br. s, 1H), 7.1-7.4 (m, 10H).

Step 2: (2S,3S)-3-Benzyloxycarbonylamino-1-t-butoxycarbonyl-2-phenylpiperidine To a solution of (2S,3S)-3-benzyloxycarbonylamino-2-phenylpiperidine (210 mg, 0.68 mmole) in methylene chloride (10 mL) at room temperature was added diisopropylethylamine (0.35 mL, 2.0 mmole) and di-t-butyl dicarbonate (221 mg, 1.0 mmole). The reaction was stirred for 16 hours and an additional aliquot of di-t-butyl dicarbonate (221 mg) was added. After stirring for another 2 days, the reaction was diluted with methylene chloride and quenched by addition of water. The mixture was separated and the aqueous was reextracted with 2 additional aliquots of methylene chloride. The organic layers were successively washed with a portion of brine, dried over sodium sulfate, combined and evaporated. The residue was purified by flash chromatography (50% ethyl acetate in hexanes) to afford 248 mg (90%) of the title compound. NMR (CDCl$_3$): δ 1.30 (s, 9H), 1.5-1.8 (m, 2H), 1.8-2.0 (m, 2H), 3.15 (m, 1H), 3.94.2 (m, 2H), 4.32 (d, J=9H), 5.05 (s, 2H), 5.30 (m, 1H), 7.2-7.4 (m, 10H).

Step 3: (2S,3S)-3-Amino-1-t-butoxycarbonyl-2-phenylpiperidine

A solution of (2S,3S)-3-benzyloxycarbonylamino-1-t-butoxy-carbonyl-2-phenylpiperidine (240 mg, 0.59 mmole) in methanol (5 mL) was hydrogenated with 10% palladium on carbon (25 mg) under balloon pressure for 2 hours. The catalyst was removed by filtration and the solvent was evaporated to give 151 mg of title compound. This was used directly in the next step.

Step 4: (2S,3S)-1-t-Butoxycarbonyl-2-phenyl-3-[2-hydroxy-5-(5'-trifluoro-methyltetrazo-1-yl)phenylmethylene-amino]piperidine A solution of (2S,3S)-3-amino-1-t-butoxycarbonyl-2-phenylpiperidine (151 mg, 0.55 mmole), 2-hydroxy-5-(5'-trifluoro-methyltetrazo-1-yl)benzaldehyde (94 mg, 0.36 mmole) (prepared as described in Example 1) and acetic acid (0.034 mL, 0.58 mmole) in dichloroethane (4 mL) was stirred at room temperature for 5 minutes before sodium triacetoxyborohydride (154 mg, 0.73 mmole) was added. After stirring for 3 days, the reaction was poured into a saturated solution of sodium carbonate and was extracted with three portions of methylene chloride. The organic layers were successively washed with a portion of brine, dried over sodium sulfate, combined and evaporated. The residue was purified by flash chromatography (25% ethyl acetate in hexanes) to afford 165 mg (87%) of the title compound. NMR (CDCl$_3$): δ 1.35 (s, 9H), 1.5-1.7 (m, 2H), 1.7-1.9 (m, 1H), 1.9-2.0 (m, 1H), 2.0-2.2 (m, 1H), 3.15 (m, 2H), 3.9-4.2 (s and m, 3H), 5.45 (br. s, 1H), 6.96 (d, J=9 Hz, 1H), 7.05 (d, J=2.5 Hz, 1H), 7.21 (dd, J=2.5 and 9 Hz), 7.25-7.4 (m, 3H), 7.45 (d, J=7 Hz, 2H).

EXAMPLE 3

Synthesis of [$^{18}$F][2-fluorodideuteromethoxy-5-(5-methyl-tetrarol-1-yl)-benzyl]-([2S,3S]-2-phenyl-piperidin-3-yl)-amine The title compound is prepared essentially as outlined below.

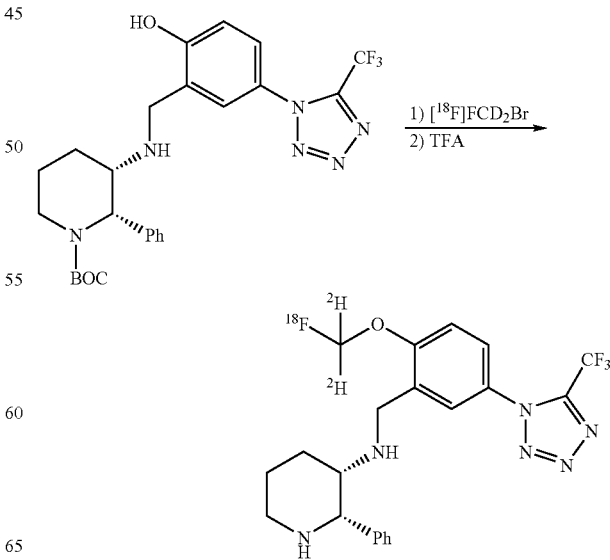

$^{18}$F$^-$ is obtained via the nuclear reaction $^{18}$O(p,n)$^{18}$F. This is achieved by bombarding a silver target containing $^{18}$O enriched water with accelerated protons (17 MeV). The $^{18}$F$^-$ is loaded onto a resin for transport. The resin is eluted with 1.5 mL of an 80:20 acetonitrile:aqueous potassium oxalate solution which is made by adding 0.05 mL of a solution of 200 mg of potassium oxalate/3 mg of potassium carbonate/5 mL of H$_2$O to 0.25 mL of H$_2$O and diluting with 12 mL of acetonitrile. To this is added 0.2 mL of a Kryptofix222 solution (36 mg/mL acetonitrile) and the acetonitrile:H$_2$O is removed at 95° C. under an argon flow and vacuum. An additional 3×0.7 mL aliquots of acetonitrile are used to dry the $^{18}$F$^-$. The oil bath is lowered and after ~1 minute a solution of 0.05 mL of CD$_2$Br$_2$ in 1 mL of acetonitrile is added, the oil bath is raised and an argon flow is used to distill the [$^{18}$F]FCD$_2$Br that forms into a vial at 0° C. that contains 0.3 mg of (2S,3S)-1-t-butoxycarbonyl-2-phenyl-3-[2-hydroxy-5-(5'-trifluoro-methyltetrazo-1-yl)phenylmethylene-amino]-piperidine) in 0.2 mL of DMF and ~1-2 mg of cesium carbonate. After the amount of radioactivity in the reaction vial peaks, the distillation is stopped and the reaction vial is heated at 100° C. for 7 minutes. The DMF is removed over five minutes using an argon flow at 100° C. and 0.1 mL of TFA is then added and allowed to sit at 100° C. for 30 seconds. The reaction mixture is diluted with 0.2 mL of ethanol and 0.6 mL of H$_2$O and purified by preparative HPLC [Waters C18 µBondapak, 7.8×300 mm, 3 mL/minute, 20 minute linear gradient 20:80 to 90:10 acetonitrile:H$_2$O (95:5:0.1 H$_2$O:MeCN:TFA)]. The product elutes at ~12 minutes.

EXAMPLE 4

Synthesis of [2-Fluoroethoxy-5-(5-trifluoromethyl-tetrazol-1-yl)-benzyl]-([2S,3S]-2-phenylpiperidin-3-yl)amine The title compound is prepared essentially as outlined below.

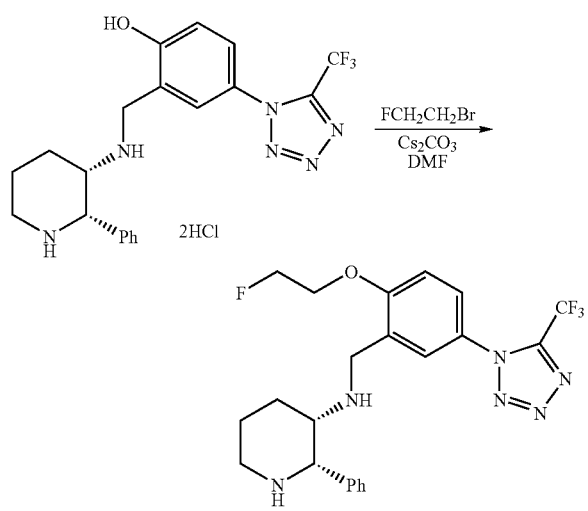

A room temperature solution of (2S,3S)-2-phenyl-3-[2-hydroxy-5-(5'-trifluoro-methyltetrazo-1-yl)phenylmethylene-amino]-piperidine), HCl salt (50 mg, 0.102 mmol) in DMF (2 mL) was treated with cesium carbonate (230 mg, 0.714 mmol). After stirring for several minutes, bromofluoroethane (9 µL, 0.122 mmol) was added and the reaction was stirred at room temperature overnight giving a yellow slurry. The reaction was diluted with aqueous saturated NH$_4$Cl/brine/H$_2$O and ethyl acetate. The layers were separated and the aqueous layer was extracted with ethyl acetate. The organic layers were combined, washed with H$_2$O, dried over MgSO$_4$, filtered and concentrated in vacuo to give 44 mg of a yellow oil. Purification by rotary chromatography (5% MeOH/EtOAc to 10% MeOH/EtOAc) gave 33.2 mg (70%) of [2-Fluoroethoxy-5-(5-trifluoromethyl-tetrazol-1-yl)-benzyl]-([2S,3S]-2-phenyl-piperidin-3-yl)-amine: $^1$H NMR (δ, CDCl$_3$): 7.25 (2H, m), 7.17 (1H, d×d, J=8.7 Hz, 2.8 Hz), 7.14 (2H, m), 7.02 (1H, m), 6.87 (1H, d, J=2.8 Hz), 6.82 (1H, d, J=8.7 Hz), 4.64 (1H, m), 4.63 (1H, m), 4.2-4.0 (2H, m), 3.87 (1H, d, J=2.4 Hz), 3.75 (1H, d, J=16 Hz), 3.58 (1H, d, J=16 Hz), 3.25 (1H, m), 2.80 (1H, m), 2.74 (1H, m), 2.10 (1H, m), 1.89 (1H, m), 1.59 (1H, m), 1.48 (1H, m). MS m/z (relative intensity) for C$_{22}$H$_{24}$F$_4$N$_6$O: 465 (M+1, 100%).

EXAMPLE 5

Synthesis of [$^{18}$F][2-Fluoroethoxy-5-(5-trifluoromethyl-tetrazol-1-yl)-benzyl]-([2S,3S]-2-phenyl-piperidin-3-yl)amine The title compound is prepared essentially as outlined below.

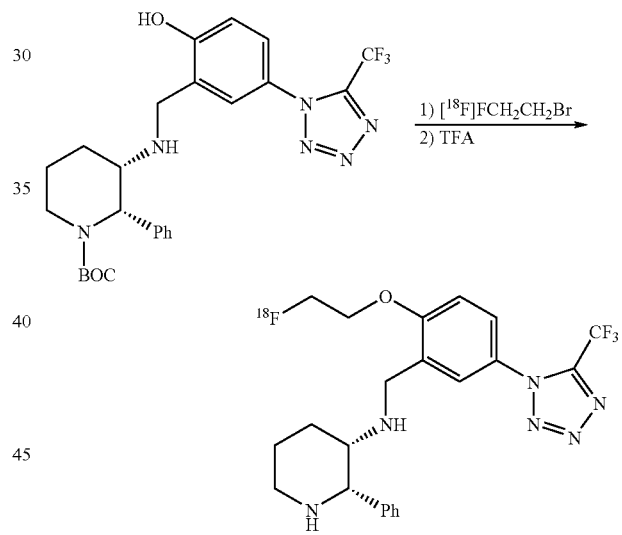

$^{18}$F$^-$ is obtained via the nuclear reaction $^{18}$O(p,n)$^{18}$F. This is achieved by bombarding a silver target containing $^{18}$O enriched water with accelerated protons (17 MeV). The $^{18}$F$^-$ is loaded onto a resin and transported to the laboratory. The resin is eluted with 1.5 mL of an 80:20 acetonitrile:aqueous potassium oxalate solution which is made by adding 0.05 mL of a solution of 200 mg of potassium oxalate/3 mg of potassium carbonate/5 mL of H$_2$O to 0.25 mL of H$_2$O and diluting with 12 mL of acetonitrile. To this is added 0.2 mL of a Kryptofix222 solution (36 mg/mL acetonitrile) and the acetonitrile:H$_2$O is removed at 120° C. under an argon flow and vacuum. An additional 3×0.7 mL aliquots of acetonitrile are used to dry the $^{18}$F$^-$. The oil bath is lowered and after ~30 seconds a solution of 0.02 mL of bromoethyl triflate (Dae Yoon Chi, Michael R Kilbourn, John A Katzenellenbogen, Michael J Welch, *J. Org. Chem.,* 1987, 52(4), 658-664) in 0.7 mL of o-dichlorobenzene is added, the oil bath is raised and an argon flow is used to distill the [$^{18}$F]

FCH$_2$CH$_2$Br that forms into a vial at 0° C. that contains 0.3 mg of (2S,3S)-1-t-butoxycarbonyl-2-phenyl-3-[2-hydroxy-5-(5'-trifluoro-methyltetrazo-1-yl)phenylmethylene-amino]-piperidine) in 0.2 mL of DMF and ~1-2 mg of cesium carbonate. After the amount of radioactivity in the reaction vial peaks, the distillation is stopped and the reaction vial is heated at 110° C. for 10 minutes. The DMF is removed over five minutes using an argon flow at 110° C. and 0.1 mL of TFA is then added and allowed to sit at 110° C. for 30 seconds. The reaction mixture is diluted with 0.2 mL of ethanol and 0.6 mL of H$_2$O and purified by preparative HPLC [Waters C18 µBondapak, 7.8×300 mm, 3 mL/minute, 20 minute linear gradient 20:80 to 90:10 acetonitrile:H$_2$O (95:5:0.1 H$_2$O:MeCN:TFA)]. The product elutes at ~12 minutes.

EXAMPLE 6

Plasma Half-Life of [$^{18}$F][2-Fluoromethoxy-5-(5-trifluoromethyl-tetrazol-1-yl)-benzyl]-([2S,3S]-2-phenyl-piperidin-3-yl)-amine To compare the plasma half-life of [$^{18}$F][2-fluoromethoxy-5-(5-trifluoromethyl-tetrazol-1-yl)-benzyl]-([2S,3S]-2-phenyl-piperidin-3-yl)-amine (Compound A) and [$^{18}$F][2-fluorodideuteromethoxy-5-(5-trifluoromethyl-tetrazol-1-yl)-benzyl]-([2S,3S]-2-phenyl-piperidin-3-yl)-amine (Compound B) in rhesus monkey, ~5 mCi of each radiotracer (in saline) was injected by iv into an anesthetized monkey. At various time points, whole blood was drawn, mixed with 0.02 mL of acetonitrile and centrifuged for 3-5 minutes at 5000 rpm. A 0.02 mL aliquot of the acetonitrile extract was spotted on a 5×7 cm TLC plate along with the cold standard and developed using 60:40:0.1 ethyl acetate:methanol:triethylamine. The TLC plate was cut into four sections pertaining to the origin, to determine the amount of fluoride present, the section between the origin and where the standard eluted, to determine polar metabolites, the section where the parent compound eluted, to determine the amount of parent compound remaining, and the area between the parent compound and the solvent front for nonpolar metabolites. The TLC strips were then counted in a gamma counter to determine the number of counts for each section of TLC plate. The percentage of the total counts that were due to the remaining parent compound was determined. At all time points examined there is more of the deuterated tracer remaining in the plasma than the protonated tracer, and at the end of the experiment (3 hours), there is twice as much of the deuterated tracer remaining. With the higher prolonged plasma levels of the deuterated tracer, more time is available for a larger specific signal to develop, and for the tracer to accumulate in brain regions that have a low receptor concentration and could be difficult to image using the protonated tracer.

TABLE 1

Percent of parent tracer remaining in monkey plasma

| Time (minutes) | % Compound A remaining | % Compound B remaining |
|---|---|---|
| 5 | 72 | 91 |
| 15 | 55 | 87 |
| 30 | 38 | 75 |
| 45 | 35 | 39 |
| 60 | 25 | 41 |
| 120 | 16 | 23 |
| 180 | 9 | 20 |

EXAMPLE 7

"Chaseability" of [$^{18}$F][2-Fluoroethoxy-5-(5-trifluoromethyl-tetrazol-1-yl)-benzyl]-([2S,3S]-2-phenyl-piperidin-3-yl)-amine compared to [$^{18}$F][2-Fluorodideutero-methoxy-5-(5-trifluoromethyl-tetrazol-1-yl)-benzyl]-([2S,3S]-2-phenyl-piperidin-3-yl)-amine Table 2 shows a comparison of [$^{18}$F][2-fluorodideuteromethoxy-5-(5-trifluoromethyl-tetrazol-1-yl)-benzyl]-([2S, 3S]-2-phenyl-piperidin-3-yl)-amine (Compound B) compared to [$^{18}$F][2-fluoroethoxy-5-(5-trifluoromethyl-tetrazol-1-yl)-benzyl]-([2S,3S]-2-phenyl-piperidin-3-yl)-amine (Compound C) in a chase study using an unlabelled NK1 antagonist in the same monkey. A bolus of an unlabelled NK1 antagonist was administered 180 minutes after a bolus injection of either tracer. From the resulting images, regions of interest were drawn to determine the amount of radioactivity present in different brain regions. As shown in Table 2, in the striatum the fluoroethoxy compound begins to chase, ie is displaced from the receptor by the unlabelled antagonist, almost immediately while the dideuterofluoromethoxy analog doesn't begin to chase until about 30 minutes after administration of the unlabelled antagonist. Also, using the 70% level of chase as a comparison (30% remaining specific binding), the fluoroethoxy compound reaches this level ~50 minutes before the dideuterofluoromethoxy analog reaches this same level. Because the fluoroethoxy compound [$^{18}$F][2-fluoroethoxy-5-(5-trifluoromethyl-tetrazol-1-yl)-benzyl]-([2S,3S]-2-phenyl-piperidin-3-yl)-amine chases from the striatum faster than the fluoromethoxy analog, a more accurate picture of what the true receptor occupancy is can be obtained using the fluoroethoxy analog.

TABLE 2

Remaining Specific Binding* in Rhesus Monkey after 1 mpk Chase at 180 Minutes with an NK1 Antagonist

| Time (minutes) | [$^{18}$F]Compound C | [$^{18}$F]Compound B |
|---|---|---|
| 195 | ~85% | ~96% |
| 205 | ~55% | ~85% |
| 220 | ~30% |  |
| 230 |  | ~55% |
| 270 |  | ~30% |

*Remaining Specific Binding = 100% * [specific binding(time) − specific binding (180 min)]/specific binding (180 min).
Specific binding = counts in striatum − counts in cerebellum.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

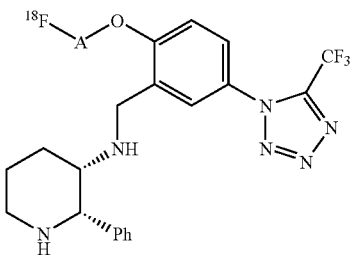

wherein:
A is —CD$_2$— or —CH$_2$CH$_2$—;
or a pharmaceutically acceptable salt thereof.

2. A compound which is:
[$^{18}$F][2-fluorodideuteromethoxy-5-(5-trifluoromethyl-tetrazol-1-yl)-benzyl]-([2S,3S]-2-phenyl-piperidin-3-yl)-amine;
or a pharmaceutically acceptable salt thereof.

3. A compound which is:
[$^{18}$F][3-fluoroethoxy-5-(5-trifluoromethyl-tetrazol-1-yl)-benzyl]-([2S,3S]-2-phenyl-piperidin-3-yl)-amine;
or a pharmaceutically acceptable salt thereof.

4. A radiopharmaceutical composition which comprises the compound of claim 1 and a pharmaceutically acceptable carrier or excipient.

5. A method for the imaging of neurokinin-1 receptor in the brain in a mammal which comprises administering to a mammal in need of such diagnostic imaging an effective amount of the compound of claim 1, and obtaining an image of the brain in the mammal using positron emission tomography.

6. The method of claim 5 wherein the mammal is a human.

* * * * *